US006486104B2

(12) United States Patent
Patzer et al.

(10) Patent No.: US 6,486,104 B2
(45) Date of Patent: Nov. 26, 2002

(54) WIPE FOR OBJECTS THAT ARE TO BE PLACED IN A CHILD'S MOUTH

(76) Inventors: William R. Patzer, 8113 E. Del Acero, Scottsdale, AZ (US) 85258; Victoria Patzer, 8113 E. Del Acero, Scottsdale, AZ (US) 85258; Kenneth Coleman, 3829 W. Folley St., Chandler, AZ (US) 85226

( * ) Notice: Subject to any disclaimer, the term of this patent is extended or adjusted under 35 U.S.C. 154(b) by 16 days.

(21) Appl. No.: 09/733,789

(22) Filed: Dec. 11, 2000

(65) Prior Publication Data

US 2002/0107157 A1 Aug. 8, 2002

(51) Int. Cl.[7] .............................. C11D 3/48; C11D 1/66
(52) U.S. Cl. ...................... 510/111; 510/130; 510/218; 510/235; 510/253; 510/356; 510/421
(58) Field of Search ................................ 510/111, 130, 510/218, 235, 253, 356, 421

(56) References Cited

U.S. PATENT DOCUMENTS

| | | | | |
|---|---|---|---|---|
| 4,140,649 A | * | 2/1979 | Bossert et al. .............. 252/105 |
| 5,286,538 A | * | 2/1994 | Pearlstein et al. .......... 428/34.2 |
| 5,320,772 A | * | 6/1994 | Tricca ......................... 252/160 |
| 5,376,391 A | * | 12/1994 | Nisperos-Carriedo et al. ... 426/102 |
| 5,500,048 A | * | 3/1996 | Murch et al. ................... 134/6 |
| 5,728,690 A | * | 3/1998 | Chen .......................... 514/179 |
| 5,874,067 A | * | 2/1999 | Lucas et al. ................... 424/65 |
| 6,258,368 B1 | * | 7/2001 | Beerse et al. ................ 424/404 |

* cited by examiner

Primary Examiner—Charles Boyer
(74) Attorney, Agent, or Firm—Jeffrey Weiss; Harry M. Weiss; Weiss, Moy & Harris, P.C.

(57) ABSTRACT

A portable wipe product for use in cleaning objects, such as pacifiers, bottles, teething objects, and cups that are to be placed in a child's mouth. The wipes are dispensed from a portable dispenser. The wipes are covered with an aqueous mixture that, in its basic form, includes purified water, one of an emulsifier and a surfactant, a moisture preserving agent, a chelator, a preservative, and an acidulant. Flavoring and an anti-oxidant may also be added.

31 Claims, 2 Drawing Sheets

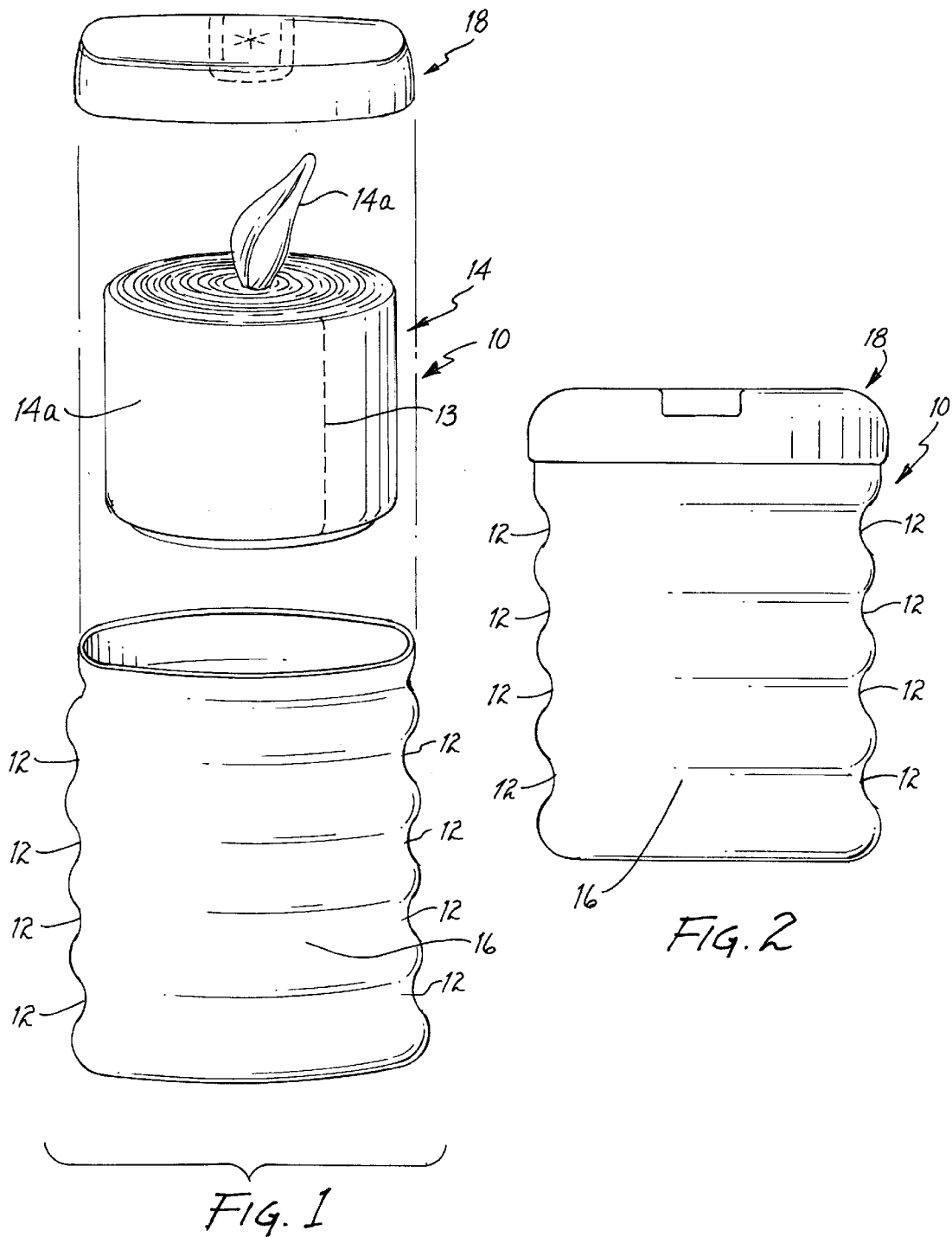

WIPE FOR OBJECTS THAT ARE TO BE PLACED IN A CHILD'S MOUTH

BACKGROUND OF THE INVENTION

1. Field of Invention

This invention relates generally to wipe products and, more specifically, to a wipe for cleaning objects such as pacifiers, nipples, teething objects, and cups that a child places in his or her mouth.

2. Background of the Invention

Virtually all parents of small children have experienced the frustration of having a pacifier, bottle, or like object fall to the ground and become dirty—making the object unsuitable to be placed in a child's mouth, even though the child may be desperately in need of that object. In such instances, parents are often forced to choose between allowing the child to cry, allowing the child to place a dirty object in his or her mouth, wiping the object on an article of clothing (e.g., pant leg or shirt), "cleaning" the object in the parent's mouth, or other unsatisfactory solutions. A parent may on occasion be tempted to use a diaper wipe for such a purpose, but chemicals present in such wipes—including fragrances, perfumes, alcohols, and oils—make them unhealthy for such use or at least bad-tasting to the child.

A proper washing of the object in warm, soapy water can be effective; however, water is not always readily available to a parent in such situations. Thus, a parent travelling in a car, seated in a theater, or otherwise distant from a sink or water fountain may not be able to clean the object in this manner. Moreover, even where a water source is available, the running of water over the object alone may not suffice to remove dirt covering the object—a wiping action of some kind may be necessary.

A need therefore existed for a portable wipe product to be used to clean objects that are placed in a child's mouth. The wipe must not be harmful to the child, and moreover must not be foul-tasting to the child. Preferably, the wipe product should be flavored so as to provide an appealing scent and so as not to leave any actual taste on the object—while not leaving an actual taste on the object that could lead an infant to develop a like or dislike to the wipe product. The present invention satisfies these needs and provides other, related, advantages.

SUMMARY OF THE INVENTION

It is an object of the present invention to provide a portable wipe product for use in cleaning objects to be placed in a child's mouth.

It is a further object of the present invention to provide a portable wipe product for use in cleaning objects to be placed in a child's mouth, which product will be harmless and non-offensive in taste.

It is a still further object of the present invention to provide a portable wipe product for use in cleaning objects to be placed in a child's mouth which product is lightly flavored so as to provide a pleasant scent and neutral taste to a child when used on an object.

BRIEF DESCRIPTION OF THE PREFERRED EMBODIMENTS

In accordance with one embodiment of the present invention, a wipe product for cleaning objects to be placed in a child's mouth is disclosed. The wipe product comprises, in combination: a dispenser; a plurality of wipes located within the dispenser and adapted to be dispensed through an opening in the dispenser; wherein the plurality of wipes is treated with a composition comprising, in combination: water; one of an emulsifier and a surfactant; a moisture preserving agent; a chelator; a preservative; and an acidulant.

In accordance with another embodiment of the present invention, a wipe product for cleaning objects to be placed in a child's mouth is disclosed. The wipe product comprises, in combination: a dispenser; a plurality of wipes located within the dispenser and adapted to be dispensed through an opening in the dispenser; wherein the plurality of wipes is treated with a composition comprising, in combination: water; wherein the water is purified using one of an ultraviolet, de-ionizing and reverse osmosis process; one of an emulsifier and a surfactant; wherein the one of an emulsifier and a surfactant is polysorbate 80; a moisture preserving agent; wherein the moisture preserving agent is glycerine; a chelator; wherein the chelator is sodium citrate; a preservative; and wherein the preservative is sodium benzoate; an acidulant; wherein the acidulant is citric acid.

In accordance with still another embodiment of the present invention, a wipe product for cleaning objects to be placed in a child's mouth is disclosed. The wipe product comprises, in combination: a dispenser; a plurality of wipes located within the dispenser and adapted to be dispensed through an opening in the dispenser; wherein the plurality of wipes is treated with a composition consisting of: water; wherein the water is purified using one of an ultraviolet and reverse osmosis process; one of an emulsifier and a surfactant; wherein the one of an emulsifier and a surfactant is polysorbate 80; a moisture preserving agent; wherein the moisture preserving agent is glycerine; a chelator; wherein the chelator is sodium citrate; a preservative; and wherein the preservative is sodium benzoate; an acidulant; wherein the acidulant is citric acid.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 1 is a front, exploded view of a wipe dispenser of the present invention.

FIG. 2 is a front view of an assembled wipe dispenser of the present invention.

DETAILED DESCRIPTION OF THE PREFERRED EMBODIMENTS

Figure 3:
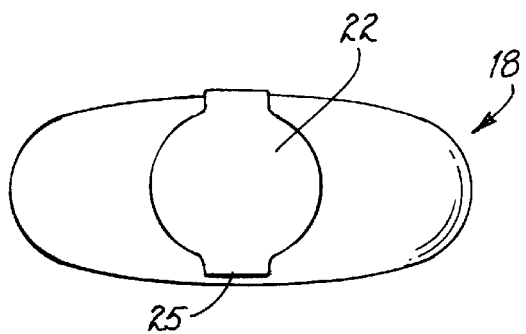
FIG. 3 is a top view of the wipe dispenser of the present invention, in a closed position.
Figure 4:
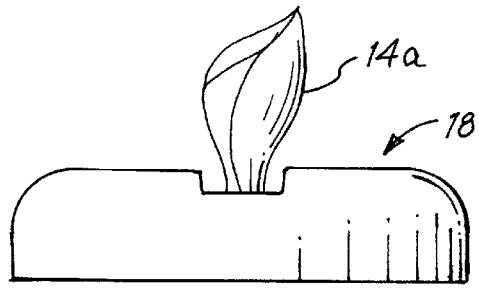
FIG. 4 is a front view of the top portion of the wipe dispenser of the present invention, with a wipe extending therethrough.

The present invention is concerned with a wipe product, for cleaning objects—including but not limited to bottle nipples, pacifiers, teething objects, and cups that a child puts into his or her mouth. The purpose of the wipe product is to clean off dirt and the like from the surface of the object, when the user finds himself or herself in a setting where there is no ready access to running water or other proper washing facility.

Referring to FIGS. 1 and 2, the wipe dispenser 10 of the present invention is shown. Preferably, the dispenser 10 has a plurality of indented regions 12 along the sides thereof, so as to make it easier for a user to identify by feel and securely grip the dispenser 10 and hold it in position while the user removes wipes 14. The wipes 14 preferably comprise a roll of individual wipes 14a, separated by perforations 13 to permit the tearing off of individual wipes 14a for use. However, it would also be possible, without departing from the spirit or scope of the present invention, to package individual wipes 14a in a non-linked manner, in a dispenser permitting their removal one at a time—as is the case with many diaper wipe wipe/dispenser combinations.

Figure 5:
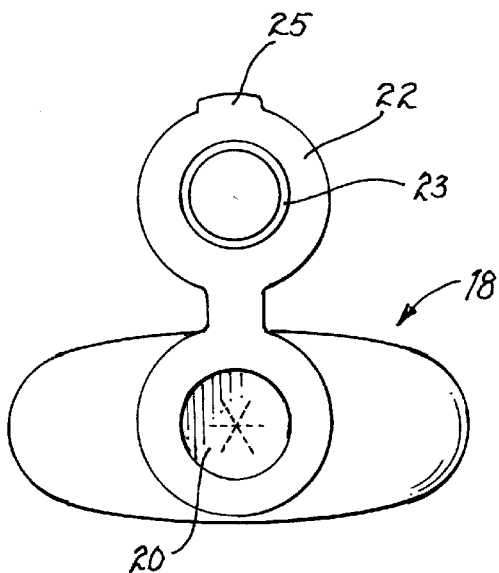
FIG. 5 is a top view of the wipe dispenser of the present invention, in an open position.

The dispenser 10 further comprises a main receptacle 16, capped by a top 18, removably fitted in a snug manner to the main receptacle 16. Referring now to FIG. 5, the top 18 comprises an opening 20, dimensioned to permit individual wipes 14a to be pulled therethrough. The opening 20 is preferably recessed within the top 18, and is covered with an attached lid 22, which lid 22 features a raised annulus 23 dimensioned to fit in a snug manner within the recessed opening 20 and a projecting tab 25 extending outward therefrom. The lid 22 may be snapped open when a user desires to access the wipes 14a within the dispenser 10 by the user clasping the projecting tab 25 and pulling the lid 22 open, and snapped closed when the user has completed the task of accessing the wipes 14a. Sufficient space should be provided within the underside of the lid 22 within the area bounded by the annulus 23 to permit a small portion of a wipe 14a to protrude through the opening 20, yet still to be retained within the lid 22 when it is in a closed position. In this manner, a user will not need to remove the top 18 to "restart" the role of wipes 14 for each new use of the dispenser 10.

Figure 6:
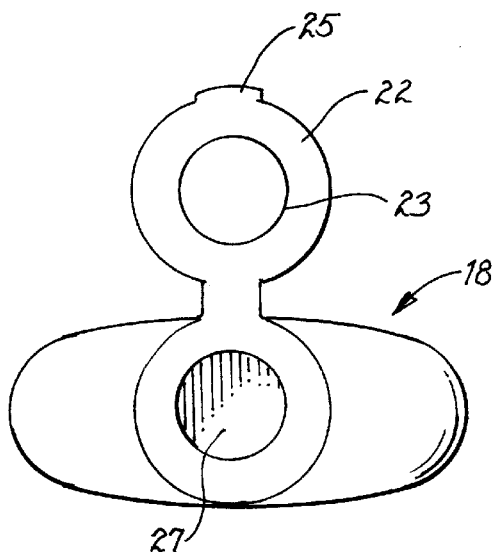
FIG. 6 is a top view of the wipe dispenser of the present invention, with a seal in place covering the opening.

Referring now to FIG. 6, preferably, the opening 20 is covered with a removable, foil-type covering 27. The purpose of the covering 27 is to maintain the moistness of the wipes 14 during the period following manufacture and before sale and use, so that when a user removes the covering 27 to commence use of the wipes 14, the wipes 14 will be in an appropriately moist condition. The covering 27 is discarded after removal. It may be possible to preserve moistness in other manners known in the art, by, for example, placing a covering at the top of the main receptacle 16, to be removed prior to use, or by encasing the entire dispenser 10 in a wrap of some type.

The wipes 14 are preferably comprised of a synthetic blend of materials. In the preferred embodiment, the wipes 14 comprise eighty percent rayon and twenty percent polypropylene. A synthetic wipe is preferred over natural compositions such as wood or cellulose because the preservative included in the treating composition—discussed below—is food grade and not as strong as non-food grade preservatives. If a natural composition for the wipes 14 were used with a food grade preservative, the result would likely be increased mould growth.

The wipes 14 are coated with an aqueous cleaner mixture to make them suitable for washing objects to be placed into a child's mouth. (An aqueous cleaner mixture is preferred to a powder, given the potential that a powder can cause lung damage or eye abrasion to a child.) The foreign matter to be washed from such objects ranges from simple dirt and dust from floors to greases and oils from automobile and garage floors, and further includes foodstuffs and pet pawing.

In one embodiment, the mixture preferably comprises, generally: (a) water, preferably ultraviolet, de-ionized or reverse osmosis processed water (with ultraviolet purified water being preferred); (b) an emulsifier or a surfactant, preferably polysorbate 80 (and in particular preferably polysorbate 80K, which is kosher and therefore lacks animal products); (c) a moisture preserving agent, preferably glycerine; (d) a chelator, preferably sodium citrate; (e) a preservative, preferably sodium benzoate; and (f) an acidulant, preferably citric acid.

The amounts by weight of each component of the mixture may be varied somewhat, and in the preferred embodiment is as follows:

In another embodiment, the mixture further includes a flavoring agent, so as to impart a pleasing scent and neutral flavor to the wipe and thus on to the object to be cleaned—without leaving a taste for which an infant may develop a like or dislike. The flavor can be, for example, a fruit flavor, an artificial flavor, or any desired flavor. Apple flavoring appears to be particularly desirable, given the affinity that many babies have for apple juice. Peach flavoring, other fruit flavors, or other flavorings could also be used.

In still another embodiment, an anti-oxidant is added. The anti-oxidant could be Vitamin C or Vitamin E. The anti-oxidant acts to prolong the shelf-life of the product by preventing its oxidation. It particularly slows the oxidation of the polysorbate 80 and, if flavoring is added, prolongs the flavor by slowing the breakdown of oils present therein.

We turn now to a discussion of each individual component member of the basic ingredients of the mixture. The water, of course, imparts moisture to the wipes 14, so as to permit the use of the wipes 14 in a washing activity. It is preferred to use water that has been purified using an ultraviolet process—although de-ionization, reverse osmosis, or other purifying processes may be used—so as not to inadvertently introduce any bacteria into the wipes 14 and from there to the object to be cleaned.

The emulsifier or surfactant is needed to permit oils that are to removed from the object to be cleaned to mix with the water in the wipes 14. The preferred emulsifier/surfactant is polysorbate 80, sometimes referred to as "tween 80," and in particular Polysorbate 80K. Polysorbate 80 is derived from vegetable oil and further has a long history in the food industry. Polysorbate 80K is preferred because it is kosher and therefore lacks animal products.

The moisture preserving agent helps maintain the water content of the wipes 14, and gives the wipes 14 the feeling of being wet even as they begin to dry out. The preferred moisture preserving agent is glycerine, a sweet-tasting, corn-oil derived product with a safe history in the baking industry, in medicines and cosmetics. Glycerine also has some cleaning properties.

The chelator serves the purpose of helping the wipes 14 to lift minerals and dirt from the object, by forming a chelate with such matter. The preferred chelator is sodium citrate, which also acts as a degreasor. Sodium citrate has been used for many years in soft drinks, cheese, and myriad other foodstuffs.

The preservative preserves the freshness of the wipes 14, and acts to inhibit microbial growth on the wipes 14. The preferred preservative is sodium benzoate. It is a long established food grade preservative, generally allowed up to 1 part per 1,000 in foodstuffs.

The acidulant is added to adjust the pH of the mixture downward to about 4.25. This serves essentially two purposes. First, without the addition of an acidulant, the mixture would tend to have a high pH, making it relatively unpalatable to humans. Second, a pH within this range is optimal for activation of the preservative—at a higher pH, the sodium benzoate will not be effective as an anti-microbial agent. The preferred acidulant is citric acid, a food grade additive used widely in the soft drink industry.

Because the wipes 14 are to be used on an object that is then to be placed in the mouth of a child, it is critical that each component of the mixture be of food or pharmaceutical grade.

In the event that during use, the wipes 14 become dried out—either simply because of the age of the product or because the lid 22 is left open for too long a period of time, the wipes 14 can be refreshed and the mixture re-activated by removing the top 18 and pouring water over the wipes 14. Preferably, so as not to introduce bacteria to the wipes 14, purified water is used for this purpose.

While the invention has been particularly shown and described with reference to preferred embodiments thereof, it will be understood by those skilled in the art that the foregoing and other changes in form and details may be made therein without departing from the spirit and scope of the invention.

We claim:

1. A method for cleaning objects to be placed in a child's mouth comprising the steps of:
   providing one of a pacifier, teething object and nipple requiring cleaning;
   cleaning a surface of said one of a pacifier, teething object, and a nipple with a wipe product for cleaning objects to be placed in a child's mouth, wherein said wipe product comprises, in combination:
   a dispenser;
   a plurality of wipes located within said dispenser and adapted to be dispensed through an opening in said dispenser;
   wherein said plurality of wipes is treated with an aqueous mixture comprising, in combination:
   water;
   one of an emulsifier and a surfactant;
   a moisture preserving agent;
   a chelator;
   a preservative; and
   an acidulant.

2. The method of claim 1 wherein said water is in an amount of greater than approximately 97 percent by weight.

3. The method of claim 1 wherein said water is purified using one of an ultraviolet, de-ionizing and reverse osmosis process.

4. The method of claim 1 wherein said one of an emulsifier and a surfactant is in an amount of approximately 1.5 percent by weight.

5. The method of claim 1 wherein said one of an emulsifier and a surfactant is polysorbate 80K.

6. The method of claim 1 wherein said moisture preserving agent is in an amount of approximately 0.5 percent by weight.

7. The method of claim 1 wherein said moisture preserving agent is glycerine.

8. The method of claim 1 wherein said chelator is in an amount of approximately 0.1667 percent by weight.

9. The method of claim 1 wherein said chelator is sodium citrate.

10. The method of claim 1 wherein said preservative is in an amount of approximately 0.1 percent by weight.

11. The method of claim 1 wherein said preservative is sodium benzoate.

12. The method of claim 1 wherein said acidulant is in an amount of approximately 0.40 percent by weight.

13. The method of claim 1 wherein said acidulant is citric acid.

14. The method of claim 1 wherein said composition further comprises a flavoring.

15. The method of claim 1 wherein said flavoring is in an amount of approximately 0.40 percent by weight.

16. The method of claim 1 further comprising a removable seal covering said opening in said dispenser.

17. The method of claim 1 further comprising an anti-oxidant.

18. The method of claim 17 wherein said anti-oxidant is one of Vitamin C and Vitamin E.

19. The method of claim 1 wherein said plurality of wipes comprise a blend of synthetic materials.

20. A method for cleaning objects to be placed in a child's mouth, comprising the steps of:
    providing one of a pacifier and a nipple requiring cleaning;
    cleaning a surface of said one of a pacifier, teething object and a nipple with a wipe product for cleaning objects to be placed in a child's mouth, wherein said wipe product comprises, in combination:
    a dispenser;
    a plurality of wipes located within said dispenser and adapted to be dispensed through an opening in said dispenser;
    wherein said plurality of wipes is treated with an aqueous mixture comprising, in combination:
    water;
    wherein said water is purified using one of an ultraviolet, de-ionizing and reverse osmosis process;
    one of an emulsifier and a surfactant;
    wherein said one of an emulsifier and a surfactant is polysorbate 80;
    a moisture preserving agent;
    wherein said moisture preserving agent is glycerine;
    chelator;
    wherein said chelator is sodium citrate;
    a preservative;
    wherein said preservative is sodium benzoate; and
    an acidulant;
    wherein said acidulant is citric acid.

21. The method of claim 20 further comprising a flavoring.

22. The method of claim 20 further comprising a removable seal covering said opening in said dispenser.

23. The method of claim 20 further comprising an anti-oxidant.

24. The method of claim 23 wherein said anti-oxidant is one of Vitamin C and Vitamin E.

25. The method of claim 20 wherein said plurality of wipes comprise a blend of synthetic materials.

26. A method for cleaning objects to be placed in a child's mouth, comprising the steps of:
    providing one of a pacifier, teething object and a nipple requiring cleaning;
    cleaning a surface of said one of a pacifier, teething object and a nipple with a wipe product for cleaning objects to be placed in a child's mouth, wherein said wipe product comprises, in combination:
    a dispenser;
    a plurality of wipes located within said dispenser and adapted to be dispensed through an opening in said dispenser;

wherein said plurality of wipes is treated with an aqueous mixture consisting of:
water;
wherein said water is purified using one of an ultraviolet, de-ionizing and reverse osmosis process;
one of an emulsifier and a surfactant;
wherein said one of an emulsifier and a surfactant is polysorbate 80;
a moisture preserving agent;
wherein said moisture preserving agent is glycerine;
a chelator;
wherein said chelator is sodium citrate;
a preservative; and
wherein said preservative is sodium benzoate;
an acidulant;
wherein said acidulant is citric acid.

27. The method of claim 26 wherein said composition further consists of a flavoring.

28. The method of claim 26 further comprising a removable seal covering said opening in said dispenser.

29. The method of claim 26 further comprising an anti-oxidant.

30. The method of claim 29 wherein said anti-oxidant is one of Vitamin C and Vitamin E.

31. The method of claim 26 wherein said plurality of wipes comprise a blend of synthetic materials.

* * * * *